US000001480H

United States Statutory Invention Registration [19]

[11] Reg. Number: H1480

Luo

[43] Published: Sep. 5, 1995

[54] METHODS OF USING DYPHYLLINE FOR THE PROMOTION OF HAIR GROWTH

[75] Inventor: Xiaochun Luo, West Chester, Ohio

[73] Assignee: The Procter & Gamble Company, Cincinnati, Ohio

[21] Appl. No.: 164,600

[22] Filed: Dec. 9, 1993

[51] Int. Cl.[6] ..... A61K 9/00

[52] U.S. Cl. ..... 424/400; 424/70; 424/450; 514/258; 514/880; 514/881; 514/934

[58] Field of Search ..... 424/400, 70, DIG. 1 C, 424/DIG. 2 C, 450; 514/258, 880, 881, 934

[56] References Cited

U.S. PATENT DOCUMENTS 4,341,783 7/1982 Scheindlin ..... 424/253

FOREIGN PATENT DOCUMENTS 3801034 7/1989 Germany ..... A61K 31/52
3913245 11/1989 Germany .
62-045527 2/1987 Japan ..... A61K 7/06

OTHER PUBLICATIONS

Stuttgen, C., and D. Neumann, "Caffein and Skin", *Aztliche Kosmetologie* vol. 19, pp. 163–187 (1980).

Seiler, W. G., "Possibilities of Preserving Hair Growth and of Controlling Dandruff and Seborrhoea in the Region of the Capillitium", *Akt. Derm.* vol. 7, pp. 51–59 (1981).

Seiler, W. G., E. Bohnert, E. G. Jung, and U. Feldmann. "Local Therapy in Androgenically Caused Hair Loss", *Artzliche Kosmetologie* vol. 14, pp. 209–220 (1984).

Imokawa, G., Y. Yada, and Y. Hori., "Induction of Melanization Within Hair Bulb Melanocytes in Chinchilla Mutant by Melanogenic Stimulants", *Society for Investigative Dermatology, Inc.*, vol. 91(2), pp. 106–113 (1988).

*Primary Examiner*—Donald P. Walsh
*Assistant Examiner*—Anthony R. Chi

[57] ABSTRACT

The subject invention relates to methods for promoting hair growth in mammals comprising topical application of dyphylline or a pharmaceutically-acceptable salt thereof. The subject invention further involves topical compositions comprising dyphylline.

17 Claims, No Drawings

A statutory invention registration is not a patent. It has the defensive attributes of a patent but does not have the enforceable attributes of a patent. No article or advertisement or the like may use the term patent, or any term suggestive of a patent, when referring to a statutory invention registration. For more specific information on the rights associated with a statutory invention registration see 35 U.S.C. 157.

METHODS OF USING DYPHYLLINE FOR THE PROMOTION OF HAIR GROWTH

TECHNICAL FIELD

The subject invention relates to the field of regulating hair growth in mammalian skin. Specifically, the subject invention relates to methods for the promotion of hair growth in humans.

BACKGROUND

Society in general continues to attach a stigma to hair loss. Men and women suffer from hair loss, often resulting in self-consciousness relating to the hair loss. Domestic animals, such as cats and dogs, also suffer from hair loss. While the animal is not likely to be emotionally affected by such hair loss, its owner may be, particularly if such an animal is to be shown in various competitions. Additionally, increased hair growth in livestock such as sheep, thereby resulting in increased wool production, is also desirable. The desire for a healthy full head (or body, in the case of animals) of hair has resulted in a variety of approaches to the "curing" of hair loss.

One such approach involves the much publicized use of minoxidil (6-(1-piperidinyl)-2,4-pyrimidinediamine 3-oxide), a potent antihypertensive agent, as a hair growth promoting agent (see U.S. Pat. Nos., 3,461,461; 3,973,061; 3,464,987; and 4,139,619). Unfortunately, not all people respond to minoxidil and the efficacy level is limited in those individuals exhibiting a response.

Another approach for "curing" hair loss involves a procedure of weaving synthetic or natural hair strands into the remaining hair strands of the subject. Such a procedure is time consuming, expensive and requires follow-up re-weavings as the weaves loosen and/or the subject's existing hair strands grow. Furthermore, such a procedure does not cure hair loss, but merely masks the condition.

Another approach for treating hair loss is the use of hair plugs. This procedure involves the transplantation of terminal hair follicles from regions of normal hair growth on the subject's scalp to regions of thinning or no hair growth on the scalp. The procedure is time consuming, expensive and can be painful. Furthermore, the transplanted plugs, at least in the early stages following transplantation, produce an unnatural look to the scalp.

For the foregoing reasons, there is a need for an easily administered, efficacious agent for treating hair loss in a mammal having little or no undesirable side effects. It is an object of the subject invention to provide topical compositions for promoting hair growth and/or treating hair loss in mammalian skin or scalp. It is a further object of the subject invention to provide such compositions which are gentler and less irritating to the skin than existing compositions. It is also an object of the subject invention to provide methods for promoting hair growth and/or treating hair loss in mammalian skin or scalp.

SUMMARY OF THE INVENTION

The subject invention involves dyphylline chemical name of dyphylline and compositions comprising dyphylline. Such a compound and compositions satisfy the need for an efficacious, easily administered agent for regulating hair growth, having little or no undesirable side effects. The subject invention is also directed to a method of regulating hair growth in a mammal (e.g., humans and domestic animals) susceptible to or suffering from hair loss, comprising application of a composition of the subject invention.

The compositions of the subject invention comprise a safe and effective amount of dyphylline and a pharmaceutically-acceptable carrier.

These and other features, aspects and advantages of the subject invention will become better understood with reference to the following description and appended claims.

DETAILED DESCRIPTION OF THE INVENTION

It has been found that compositions containing dyphylline exhibit the ability to regulate hair growth in mammalian skin and scalp, without undesirable side effects, such as skin irritation, commonly associated with known compositions for regulating hair growth. While the subject invention is not limited to any particular mode of action, it is believed that dyphylline may regulate hair growth by elevating intracellular level of cyclic adenosine monophosphate, via inhibiting phosphodiesterase and activating adenosine reception on all membrane. By phosphodiesterase inhibition which results in an increase in the level of intracellular cyclic adenosine monophosphate (cAMP). Reduction of cAMP levels in the hair follicle has been linked to alopecia or hair loss.

As used herein, "dyphylline" means a compound having the structure:

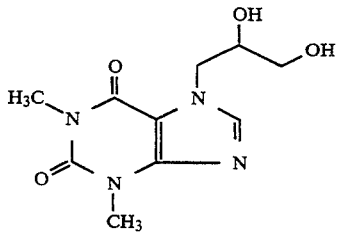

As used herein, "topical application" means directly laying on or spreading on outer skin.

As used herein, "cutaneous injection" means introduction of a substance beneath or within the skin by a hypodermic needle; preferably proximate to the site of desired response.

As used herein, "safe and effective amount" means a sufficient amount of a compound or composition to significantly induce a positive modification in the condition being treated, but low enough to avoid serious side effects.

As used herein, "comprising" means that other steps and other ingredients which do not affect the end result can be added. This term encompasses the terms "consisting of" and "consisting essentially of".

As used herein, "pharmaceutically-acceptable" means that drugs, medicaments or inert ingredients which the term describes are suitable for use in contact with the tissues of humans and lower animals without undue toxicity, incompatibility, instability, irritation, allergic response, and the like.

As used herein, "cosmetically-acceptable" means that ingredients which the term describes are suitable for use in contact with the skin of humans and lower animals without undue toxicity, incompatibility, instability, irritation, allergic response, and the like.

As used herein, "regulating hair growth" means increasing the rate of hair growth and/or inducing the formation of a greater number of hair strands, and/or increasing the diameter of the hair strand, and/or lengthening the hair strand, and/or changing the hair follicle from vellus to terminal, and/or converting follicles from telogen to anagen phase (thereby increasing the overall ratio of anagen phase follicles relative to telogen phase follicles) and/or preventing, retarding, or arresting the process of hair loss, and/or treating alopecias.

As used herein, "vellus hair follicle" means a hair follicle which produces a soft, short, and often colorless hair fiber. The size of the vellus follicle is considerably smaller than the terminal hair follicle. In an adult, vellus follicles can be found on the forehead (i.e., receding hair line area) and bald scalp beside other parts of the body.

As used herein, "terminal follicle" means a hair follicle which produces a coarse, long, and often pigmented hair follicle. The size of the terminal follicle is considerably larger, thicker in diameter and longer than the vellus follicle. In the adult, terminal follicles can be found on the scalp, axilla and pubic areas. (Chest and legs.)

As used herein, "anagen phase" refers to the period in the hair follicle growth cycle wherein the follicle is actively growing and a real hair strand is extending.

As used herein, "telogen phase" refers to the period in the hair growth cycle wherein the follicle is resting and hair strand cease extending.

Compositions useful for regulating hair growth preferably comprise from about 0.005% to about 15% of dyphylline, more preferably from about 0.1% to about 10%, more preferably still from about 1% to about 5%, more preferably still from about 1% to about 3%.

The Carrier

The compositions of the subject invention comprise a solid, semi-solid or liquid cosmetically and/or physiologically acceptable and/or pharmaceutically-acceptable carrier to enable dyphylline to be delivered to the desired target at an appropriate concentration. The carrier can itself be inert or it can possess cosmetic, physiological or pharmaceutical benefits of its own. The nature of the carrier will be dictated by the method chosen for administration of the composition. The method of administration of dyphylline composition may range from internal methods such as injection to external topical methods.

A preferred method of administration of dyphylline is by cutaneous injection. The carrier for facilitation of such administration would preferably comprise water or a saline solution, preferably an isotonic saline solution.

A more preferred method of administration of dyphylline is by topical application. Topical application is preferably achieved with compositions in the forms of lotions, solutions, ointments, sprays, tonics, creams, bars, shampoos, cream rinses, gels, sticks, mousse, pastes and the like.

Topical compositions of the subject invention can be formulated as liquids, for example as a lotion, shampoo, conditioner, mousse or milk. Such liquid compositions may be formulated for use in conjunction with an applicator such as a roll-ball applicator, a tined applicator, a pad applicator, or a spray device such as an aerosol can containing propellant, or a container fitted with a pump to dispense the liquid product, or a liquid-impregnated fabric, such as a tissue wipe.

Alternatively, the compositions of the invention can be solid or semi-solid, for example sticks, creams or gels. Such solid or semi-solid compositions may be formulated for use in conjunction with a suitable applicator or simply a tube, jar or other convenient container.

The selection of a carrier for this purpose subjects a wide range of possibilities depending on the required product form of the composition. Suitable vehicles can be classified as described hereinafter.

The term "topical carrier" refers to substances which can act as diluents, dispersants, or solvents for dyphylline which therefore ensure that it can be applied to and distributed evenly over the selected target at an appropriate concentration. The carrier is preferably one which can aid penetration of dyphylline into the skin to reach the immediate environment of the hair follicle. Topical carriers useful in compositions of the subject invention can include water as a vehicle, and/or at least one cosmetically acceptable vehicle other than water. Carriers useful in topical compositions according to the invention may include liposomes, latex latices, microspheres, cyclodextrins and various forms of microencapsulation of dyphylline. A preferred amount of penetration enhancing agent is from about 1% to about 5% of the composition.

Generally, the carrier is either organic in nature or an aqueous emulsion and capable of having dyphylline dispersed or dissolved therein. The carrier may include pharmaceutically-acceptable emollients, skin penetration enhancers, coloring agents, fragrances, emulsifiers, thickening agents, and solvents.

Topical compositions of the subject invention may be formulated as a composition comprising an emollient. Such compositions typically comprise from about 1% to about 50%, preferably from about 5% to about 20% of a topical pharmaceutically-acceptable emollient; and a safe and effective amount of dyphylline.

As used herein, "emollients" refer to materials used for the prevention or relief of dryness, as well as for the protection of the skin. A wide variety of suitable emollients are known and may be used herein. Such emollients include, but are not limited to, hydrocarbon oils and waxes, silicon oils, triglyceride fats and oils, acetoglyceride esters, ethoxylated glycerides, alkyl esters of fatty acids having 10 to 20 carbon atoms, alkenyl esters of fatty acids having 10 to 20 carbon atoms, fatty acids having 8–22 carbon atoms, fatty alcohols having 8–22 carbon atoms, fatty alcohol ethers, ether-esters, lanolin and derivatives, polyhydric alcohols and polyether derivatives, wax esters, beeswax derivatives, vegetable waxes, phospholipids, sterols, and amides. SAGARIN, COSMETICS, SCIENCE AND TECHNOLOGY, 2nd Edition, Vol. 1, pp. 32–43 (1972), incorporated herein by reference, contains numerous examples of suitable materials.

Topical compositions of the subject invention may also be formulated as a cream. Preferably the creams of the present invention comprise a safe and effective amount of dyphylline; from about 1% to about 50%, preferably from about 5% to about 25%, of an emollient; and from about 25% to about 95% water. Optionally the cream form contains a suitable emulsifier. When an emulsifier is included, it is in the composition at a level from about 1% to about 25%, preferably from about 3% to about 10%. Emulsifiers may be nonionic, anionic or cationic. Suitable emulsifiers are disclosed in, for example, U.S. Pat. No. 3,755,560, issued Aug. 28, 1973, Diekert et al.; U.S. Pat. No. 4,421,769,issued Dec. 20, 1983, Dixon et al.; and McCutheon's *Detergents and Emulsifiers,* North American Edition, pp. 317–324 (1986); the disclosures of which are incorporated herein by reference. Preferred emulsifiers are anionic or nonionic.

Topical compositions of the subject invention may also be formulated as a composition comprising a lotion. Preferably the lotions of the subject invention comprise a safe and effective amount of dyphylline; from about 1% to about 50%, preferably from about 3% to about 15% of an emollient; and from about 45% to about 85%, preferably from about 50% to about 75% water. Optionally, the lotion form may contain a suitable emulsifier, comprising from about 1% to about 50%, preferably from about 3% to about 10% of the composition. Example of suitable emulsifiers are included hereinabove in the disclosure of cream formulations.

Preferably a solution form of the present invention comprises a safe and effective amount of dyphylline, water and a suitable organic solvent. Suitable organic materials useful as the solvent or a part of a solvent system are as follows: propylene glycol, dimethyl isosorbide, N-octyl pyrrolidone, glycerin, polyethylene glycol (M.W. 200–600), polypropylene glycol (M.W. 425–2025), sorbitol esters, 1,2,6-hexanetriol, ethanol, isopropanol, diethyl tartrate, butanediol, and mixtures thereof.

Gel compositions of the present invention can be formulated by simply mixing a suitable thickening agent to the previously described solution compositions. The gel compositions preferably comprise a safe and effective amount of dyphylline; from about 5% to about 75%, preferably from about 10% to about 50%, of an organic solvent as previously described for solutions; and from about 0.1% to about 10%, preferably from about 0.5% to about 5% of the thickening agent.

Compositions of solid forms of the present invention have use as stick-type compositions intended for application to scalp or other parts of the body. Such compositions preferably comprise a safe and effective amount of dyphylline, and from about 50% to about 98%, preferably from about 60% to about 90%, of the previously described emollients. Such compositions can further comprise from about 1% to about 20%, preferably from about 5% to about 15%, of a suitable thickening agent, and optionally emulsifiers and water.

Scalp cleaning compositions useful in hair growth regulation, comprise, in addition to dyphylline, a cosmetically-acceptable surfactant. The cleaning compositions useful in the subject invention preferably contain a safe and effective amount of dyphylline and preferably from about 1% to about 90%, more preferably from about 5% to about 10%, of a cosmetically-acceptable surfactant.

The physical form of the cleansing compositions is not critical. The compositions can be, for example, formulated as toilet bars, liquids, shampoos, pastes, or mousses. Rinse-off cleansing compositions, such as shampoos, require a delivery system adequate to deposit an effective amount of dyphylline to the scalp. A preferred delivery system involves the use of insoluble complexes. For a more complete disclosure, see U.S. Pat. No. 4,835,148, Barford et al., issued May 30, 1989; incorporated herein by reference in its entirety.

The surfactant component of the compositions useful in the subject invention are selected from anionic, nonionic, zwitterionic, amphoteric and ampholytic surfactants, as well as mixtures of these surfactants. Such surfactants are well-known to those skilled in the detergency art.

The cleaning compositions useful in the subject invention can optionally contain, at their ann-established levels, materials which are conventionally used in cleansing compositions. Nonlimiting examples of possible surfactants include isoceteth-20, sodium methyl cocoyl taurate, sodium methyl oleoyl taurate, and sodium lauryl sulfate. See U.S. Pat. No. 4,800,197, to Kowcz et al., issued Jan. 24, 1989, which is incorporated herein by reference in its entirety. Examples of a broad variety of additional surfactants useful herein are described in McCutcheon's, DETERGENTS AND EMULSIFIERS, North American Edition (1986), published by Allured Publishing Corporation, which is incorporated herein by reference in its entirety.

Combination Actives

The compositions of the subject invention useful for regulating hair growth may also optionally comprise other hair growth stimulants capable of functioning in different ways to enhance the benefit of dyphylline. An example of such a substance includes, but is not limited to minoxidil, and derivatives thereof, as disclosed in U.S. Pat. Nos., 3,461,461; 3,973,061; 3,464,987; and 4,139,619; incorporated herein by reference.

Additional hair growth stimulants useful in compositions of the subject invention comprising dyphylline include the agents disclosed by the following, which are all incorporated herein by reference: U.S. Pat. No. 5,215,760, Kavoussi and Kavoussi, issued Jun. 1, 1993; U.S. Pat. No. 5,192,534, Grollier and Richoux, issued Mar. 9, 1993; U.S. Pat. No. 5,178,883, Knighton, issued Jan. 12, 1993; U.S. Pat. No. 5,177,061, Pickart, issued Jan. 5, 1993; U.S. Pat. No. 5,130,142, Wong and Warren, issued Jul. 14, 1992; U.S. Pat. No. 5,068,315, Buultjens, Colin, Jahoda and Oliver, issued Nov. 26, 1991; U.S. Pat. No. 5,091,173, Buultjens, Hellens, Oliver and Withers, issued Feb. 25, 1992; U.S. Pat. No. 5,037,643, Green, issued Aug. 6, 1991; U.S. Pat. No. 4,975,441, Gibson, issued Dec. 4, 1990; U.S. Pat. No. 4,871,839, Gibson, issued Oct. 3, 1989; U.S. Pat. No. 4,832,946, Green, issued May 23, 1989; U.S. Pat. No. 4,761,401, Couchman, issued Aug. 2, 1988; U.S. Pat. No. 4,139,619, Chidsey, issued Feb. 13, 1979; U.S. Pat. No. 3,466,364, Takahashi, issued Sep. 9, 1969; and U.S. Pat. No. 1,732,120, Christen, issued Oct. 15, 1929; PROSCAR TM (a.k.a., finasteride or (5α, 17β)-1-1-Dimethylethyl)-3-oxo-4-azaandrost-1-ene-17-carboxamide; Merck & Co.) see THE MERCK INDEX, 11th Ed., p. 1250, entry 7888; and cyproterone acetate, see THE MERCK INDEX, 11 th Ed., p. 435, entry 2781.

Delivery Methods for Topical Compositions

The topical compositions useful for the methods of the instant invention can be delivered from a variety of delivery devices. The following are two nonlimiting examples.

A. Medicated cleansing pads

The compositions useful herein can be incorporated into a medicated cleansing pad. Preferably these pads comprise from about 50% to about 75% by weight of one or more layers of nonwoven fabric material and from about 20% to about 50% by weight of a liquid composition deliverable from the nonwoven fabric material preferably comprising from about 0.01% to about 10% dyphylline, more preferably from about 0.5% to about 5% dyphylline, more preferably still from about 1% to about 3%. These pads are described in detail in U.S. Pat. Nos. 4,891,228, to Thaman et al., issued Jan. 2, 1990; and 4,891,227, to Thaman et al., issued Jan. 2, 1990; both of which are incorporated by reference.

B. Dispensing devices

The compositions useful herein can also be incorporated into and delivered from a soft-tipped or flexible dispensing device. These devices are useful for the controlled delivery of the compositions to the skin or scalp surface and have the advantage that the treatment composition itself never need be directly handled by the user. Nonlimiting examples of these devices comprise a fluid container including a mouth, an applicator, means for holding the applicator in the mouth of the container, and a normally closed pressure-responsive valve for permitting the flow of fluid from the container to the applicator upon the application of pressure to the valve. The fluid preferably contains from about 0.005% to about 15% dyphylline, more preferably from about 0.5% to about 3% dyphylline, more preferably still from about 1% to about 3%.

The valve can include a diaphragm formed from an elastically fluid impermeable material with a plurality of non-intersecting arcuate slits therein, where each slit has a base which is intersected by at least one other slit, and where each slit is out of intersecting relation with its own base, and wherein there is a means for disposing the valve in the container inside of the applicator. Examples of these applicator devices are described in U.S. Pat. No. 4,693,623, to Schwartzman, issued Sep. 15, 1987; U.S. Pat. No. 4,620,648, to Schwartzman, issued Sep. 15, 1987; U.S. Pat. No. 3,669,323, to Harker et at., issued Jun. 13, 1972; U.S. Pat. No. 3,418,055, to Schwartzman, issued Dec. 24, 1968; and U.S. Pat. No. 3,410,645, to Schwartzman, issued Nov. 12, 1968; all of which are incorporated herein by reference. Examples of applicators useful herein are commercially available from Dab-O-Matic, Mount Vernon, N.Y.

Methods for Regulating Hair Growth

The subject invention provides for the use of dyphylline for preventing hair loss. Such prophylactic application is particularly useful to individuals who have a family history of baldness. In another embodiment, the subject invention provides for the use of dyphylline for stimulating new hair growth. Preferably, dyphylline is applied to mammals in need of hair growth regulation, more preferably to mammals suffering from hair loss. The following methods of use may be used to regulate hair growth.

The compositions according to the invention are preferably intended for application by cutaneous injection. The amount of the composition and the frequency of cutaneous injection can vary widely, depending on personal needs. As an example of application by cutaneous injection, it is suggested that a composition suitable for cutaneous injection comprising dyphylline be cutaneously injected preferably from about once per day to about once every six months, more preferably from about twice per week to about twice per month. The composition for cutaneous injection will preferably administer from about 0.01 to about 1 mg of dyphylline per $cm^2$ skin receiving cutaneous injection, more preferably from about 0.02 to about 0.5 $mg/cm^2$, more preferably still from about 0.05 to about 0.1 $mg/cm^2$. The period of injections would be over a period of from about one month to the life of the subject, more preferably, in the case of humans, from about 1 month to about ten years, more preferably from about three months to about two years, more preferably still from about six months to about one year, thereby resulting in regulation of hair growth.

A more preferred method of applying the compositions according to the subject invention involves topical application to the scalp of a human subject or the skin of a domesticated animal subject to regulate hair growth, particularly where the scalp/skin is already bald or balding. The amount of the composition and the frequency of application to the hair and/or scalp/skin can vary widely, depending on the desired effect and/or personal needs, but it is suggested as an example that topical application preferably range from about 1 to about 10 times daily, more preferably from about 1 to about 6 times daily, more preferably still from about 1 to about 3 times daily, and most preferably about once per day.

The composition for topical application will preferably contain from about 0.01 to about 1,000 μg of dyphylline per $cm^2$ skin receiving the topical composition, more preferably from about 0.1 to about 600 $\mu g/cm^2$, more preferably still from about 1 to about 300 $\mu g/cm^2$, more preferably from about 100 to about 300 $\mu g/cm^2$. The period of topical application may be over the subject's life, but would preferably, in the case of a human subject, be over a period of from about one month to about ten years, more preferably from about three months to about two years, more preferably still from about six months to about one year, thereby resulting in regulation of hair growth.

In another embodiment of the subject invention, hair growth regulation is achieved by topical administration of a composition of the subject invention and oral administration of an antiandrogen (e.g., finasteride, cyproterone acetate) during the same treatment period.

Examples

The composition embodiments of the subject invention are illustrated in the following examples. All parts, percentages, and ratios used herein are by weight unless otherwise specified.

Example I

An injectable composition is prepared by combining the following components utilizing conventional mixing techniques.

| Component | Example No. 23 |
|---|---|
| Dyphylline | 2.0 |
| Sodium chloride | 0.9 |
| Sterile water for injection, USP | q.s. to 100% |

0.1 cc of the composition per $cm^2$ skin is injected at the site of desired hair regulation once every two weeks for six months to a subject resulting in new hair growth.

Examples II–IV

The following topical solutions are prepared by combining the following components utilizing conventional mixing techniques.

| Component | Example No. 24 | 25 | 26 |
|---|---|---|---|
| Dyphylline | 0.01 | 1.00 | 5.00 |
| N-octyl pyrrolidone | 1.00 | 3.00 | 5.00 |
| Perfume | 1.00 | 1.00 | 1.00 |
| Dimethyl isosorbide | | balance to 100% | |

1000 mg of the composition per 100 $cm^2$ skin is topically applied twice per day for one year to a subject resulting in new hair growth.

Examples V–VII

The following conditioning lotions are prepared by combining the following components utilizing conventional mixing techniques.

| Component | Example No. 27 | 28 | 29 |
|---|---|---|---|
| Dyphylline | 0.01 | 1.00 | 5.00 |
| Ammonium laureth sulfate | 6.00 | 6.00 | 6.00 |
| Disodium cocoamphodiacetate | 3.00 | 3.00 | 3.00 |
| Alkyl polyglucosides | 2.70 | 2.70 | 2.70 |
| Glycerine | 5.00 | 5.00 | 5.00 |
| Dimethicone copolyol | 2.00 | 2.00 | 2.00 |
| Polyol alkoxy ester | 1.20 | 1.20 | 1.20 |
| Polyquat 10 | 1.00 | 1.00 | 1.00 |
| Sodium benzoate | 0.25 | 0.25 | 0.25 |
| DNMM hydantoin* | 0.14 | 0.14 | 0.14 |
| Disodium EDTA** | 0.13 | 0.13 | 0.13 |
| Mineral oil | 4.00 | 4.00 | 4.00 |
| Myristic acid | 1.10 | 1.10 | 1.10 |
| Polyethylene glycol caprylic/capric glycerides | 2.00 | 2.00 | 2.00 |
| Titanium doxide | 0.10 | 0.10 | 0.10 |
| Perfume | 1.00 | 1.00 | 1.00 |
| Water | | balance to 100% | |

*1,3-dihydroxymethyl-3,3-dimethyl hydantoin
**ethylenediaminetetraacetic acid 1000 mg of the composition per 100 $cm^2$ skin is topically applied once per day for 6 months to a subject resulting in prevention of hair loss.

Examples VIII–X

The following shampoo compositions are prepared by combining the following components utilizing conventional mixing techniques.

| Component | Example No. 30 | 31 | 32 |
|---|---|---|---|
| Dyphylline | 0.01 | 1.00 | 5.00 |
| Ammonium laureth sulfate | 6.00 | 6.00 | 6.00 |
| Disodium cocoamphodiacetate | 3.00 | 3.00 | 3.00 |
| Alkyl polyglucosides | 2.70 | 2.70 | 2.70 |
| Glycerine | 5.00 | 5.00 | 5.00 |
| Dimethicone copolyol | 2.00 | 2.00 | 2.00 |
| Polyol alkoxy ester | 1.20 | 1.20 | 1.20 |
| Polyquat 10 | 1.00 | 1.00 | 1.00 |
| Sodium benzoate | 0.25 | 0.25 | 0.25 |
| DMDM hydantoin* | 0.14 | 0.14 | 0.14 |
| Disodium EDTA** | 0.13 | 0.13 | 0.13 |
| Titanium dioxide | 0.10 | 0.10 | 0.10 |
| Perfume | 1.00 | 1.00 | 1.00 |
| Water | | balance to 100% | |

*1,3-dihydroxymethyl-3,3-dimethyl hydantoin
**ethylenediaminetetraacetic acid

This composition may be used in a conventional manner for cleaning hair, while bestowing hair growth regulation to the subject. From about 0.1 g to about 10 g of the composition is applied to hair that has been wetted, generally with water, worked through the hair and then rinsed out.

While particular embodiments of the subject invention have been described, it will be obvious to those skilled in the art that various changes and modifications of the subject invention can be made without departing from the spirit and scope of the invention. It is intended to cover, in the appended claims, all such modifications that are within the scope of the invention.

Examples XI–XIII

The following topical solutions are prepared by combining the following components utilizing conventional mixing techniques.

| Component | Example No. 33 | 34 | 35 |
|---|---|---|---|
| Dyphylline | 1.00 | 3.00 | 5.00 |
| Propylene glycol | 49.00 | 47.00 | 35.00 |
| Ethanol | 30.00 | 30.00 | 30.00 |
| Water | 20.00 | 20.00 | 30.00 |

1000 mg of the composition per 100 $cm^2$ of skin is topically applied once per day for six months to a subject resulting in new hair growth.

Examples XIV–XVII

The following vanishing creams are prepared by combining the following components utilizing conventional mixing techniques.

| Component | Example No. 36 | 37 | 38 | 39 |
|---|---|---|---|---|
| Dyphylline | 3.00 | 3.00 | 3.00 | 3.00 |
| Stearic acid | 13.00 | 7.00 | 14.00 | |
| Stearyl alcohol | 1.00 | 5.00 | | |
| Cetyl alcohol | 1.00 | 2.00 | 2.00 | |
| Glyceryl monostearate | | | | 10.00 |
| Isopropyl palmitrate | | | 2.00 | |
| Lanolin | | | | 2.00 |
| Methyl paraben | 0.10 | 0.10 | 0.10 | 0.10 |
| Sorbitan monostearate | | | 2.00 | |
| Potassium hydroxide | 0.90 | | | |
| Sodium lauryl sulfate | | 1.00 | | |
| Polysorbate 60 | | | 1.50 | |
| Stearyl colamino formyl methyl pyridinium chloride | | | | 1.50 |
| Water | | | q.s. to 100% | |

1000 mg of the composition per 100 $cm^2$ skin is topically applied twice per day for six months to a subject resulting in new hair growth.

Examples XVIII–XX

The following penetrating creams are prepared by combining the following components utilizing conventional mixing techniques.

| Component | Example No. 40 | 41 | 42 |
|---|---|---|---|
| Dyphylline | 0.01 | 1.00 | 5.00 |
| Cetearyl alcohol | 5.00 | 5.00 | 5.00 |
| Silicone oil, 200 fluid | 1.00 | 1.00 | 1.00 |
| Isopropyl myristate | 2.00 | 2.00 | 2.00 |
| Sodium stearoyl-2-lactylate | 2.00 | 2.00 | 2.00 |
| Propylene glycol | 5.00 | 5.00 | 5.00 |
| Sodium citrate | 0.2 | 0.2 | 0.2 |
| Preservative | q.s. | q.s. | q.s. |

-continued

| Component | Example No. 40 | 41 | 42 |
|---|---|---|---|
| Water | | q.s. to 100 | |

1000 mg of the composition per 100 $cm^2$ ski is topically applied once per day for one year to a subject resulting in new hair growth.

Examples XXI–XXIII

The following ion pair oil-in-water emulsions are prepared by combining the following components utilizing conventional mixing techniques.

| Component | Example No. 43 | 44 | 45 |
|---|---|---|---|
| Dyphylline | 0.01 | 1.00 | 5.00 |
| Pemuten Tr-2 | 0.30 | 0.30 | 0.30 |
| Distearyl dimethyl ammonium chloride | 0.15 | 0.15 | 0.15 |
| Mineral oil | 6.0 | 6.0 | 6.0 |
| Dimethyl isosorbide | 6.0 | 6.0 | 6.0 |
| Dioctyl malate | 6.0 | 6.0 | 6.0 |
| Cetyl alcohol | 1.0 | 1.0 | 1.0 |
| Stearyl alcohol | 1.0 | 1.0 | 1.0 |
| Triethanolamine | 0.50 | 0.50 | 0.50 |
| Water | | q.s. to 100 | |

1000 mg of the composition per 100 $cm^2$ of the skin is topically applied twice per day for six months to a subject resulting in new hair growth.

Examples XXIV–XXVI

The following liposomal dispersions are prepared by combining the following components utilizing conventional mixing techniques.

| Component | Example No. 46 | 47 |
|---|---|---|
| Dyphylline | 5.00 | 5.00 |
| Phosphatidyl choling (soy) | 5.00 | |
| Cholesterol | 0.5 | 1.00 |
| Polyoxyethylene cetylether | | 5.00 |
| Polyoxyehtylene cetyl amine | | 5.00 |
| Alpha-tocapherol | 1.0 | |
| EDTA | 0.1 | 0.1 |
| Water | q.s. to 100 | |

The reagents are blended to produce unilamillar or multilamellar vesicles by methods known to those skilled in the art. The resulting dispersions are either directly applied topically to the scalp (100 mg of composition per 100 $cm^2$ of skin) or are blended into a suitable oil-in-water emulsion carrier, e.g, those in Examples V–VII, XIV, XVI, XVIII-XX at a level of about 1–25% (w/w) and then applied topically to the scalp at a comparable dosage level.

What is claimed is:

1. A method of regulating hair growth in mammals comprising applying to a mammal in need of treatment a composition comprising:

a) a safe and effective amount of dyphylline, having the structure:

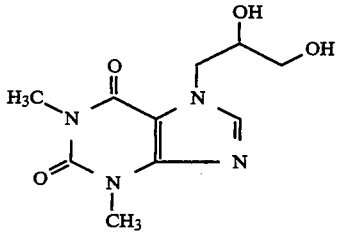

or a pharmaceutically-acceptable salt thereof; and b) a carrier.

2. The method of claim 1 wherein application of the composition is by subcutaneous injection.

3. The method of claim 1 wherein application of the composition is topical.

4. The method of claim 3 wherein the amount of dyphylline applied to the skin is from about 0.01 μg per $cm^2$ skin to about 600 μg per $cm^2$ skin.

5. The method of claim 4 wherein the amount of dyphylline applied to the skin is from about 0.1 μg per $cm^2$ skin to about 600 μg per $cm^2$ skin.

6. The method of claim 4 wherein the amount of dyphylline applied to the skin is from 1 μg per $cm^2$ skin to about 300 μg per $cm^2$ skin.

7. A fluid dispensing device comprising:

a) a fluid container with a mouth;

b) a soft, porous-tipped applicator at an end of the fluid container;

c) a means for holding the applicator in the mouth of the container; and d) a liquid composition deliverable from the fluid container through the applicator onto the skin, comprising from about 0.005% to about 15% of a compound having the structure:

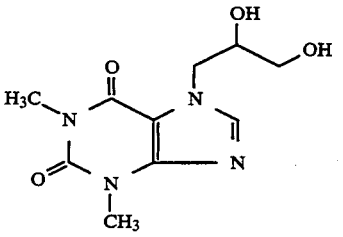

or a pharmaceutically-acceptable salt thereof.

8. The device of claim 7 wherein the liquid composition further comprises a phosphodiesterase inhibitor.

9. The device of claim 7 wherein the liquid composition comprises from about 1% to about 3% of dyphylline.

10. The device of claim 7 wherein the liquid composition further comprises cyclic adenosine monophosphate or a derivative thereof.

11. The method of claim 1 wherein the composition comprises a topical carrier comprising an emollient.

12. The method of claim 1 wherein the composition comprises from about 0.005% to about 15% dyphylline.

13. The method of claim 1 wherein the topical carrier further comprises glycerine.

14. The method of claim 13 wherein the topical carrier comprises from about 45% to about 85% water.

15. The method of claim 14 wherein the composition comprises from about 1% to about 10% dyphylline.

16. The method of claim 15 wherein the composition comprises from about 1% to about 5% dyphylline.
17. A topical composition for regulating hair growth in mammalian skin comprising:
a) a safe and effective amount of dyphylline having the structure:
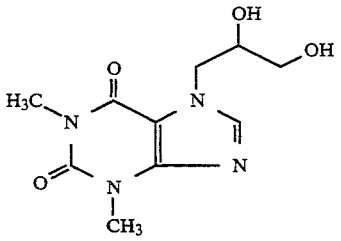
or a pharmaceutically-acceptable salt thereof; and
b) a topical carrier comprising finasteride.
* * * * *